United States Patent [19]

Rey et al.

[11] Patent Number: 4,804,383

[45] Date of Patent: Feb. 14, 1989

[54] TEMPORARY PROSTHESIS FOR TENDONS AND LIGAMENTS, AND A METHOD OF FITTING SAME

[76] Inventors: Pierre Rey, 18 rue Aristide Briand, 77400 Lagny; Jacqueline Leandri, 50 avenue de Clichy, 75018 Paris; Philippe Dahhan, 72 rue Ampére, 75017 Paris, all of France

[21] Appl. No.: 857,871

[22] Filed: May 1, 1986

[51] Int. Cl.⁴ .............................................. A61F 2/08
[52] U.S. Cl. ......................................... 623/13; 623/1; 623/66; 128/335.5; 8/137.5; 528/348
[58] Field of Search ................................ 8/137.5, 139; 128/335.5; 623/1, 11, 13, 66; 528/348

[56] References Cited

U.S. PATENT DOCUMENTS

| | | | |
|---|---|---|---|
| 3,300,450 | 1/1967 | Clay | 8/137.5 |
| 3,476,504 | 11/1969 | Case et al. | 8/139 |
| 4,164,794 | 8/1979 | Spector et al. | 3/912 |
| 4,167,538 | 9/1979 | Taniguchi et al. | 428/375 |
| 4,329,185 | 5/1982 | Dimov et al. | 623/66 |
| 4,362,681 | 12/1982 | Spector et al. | 264/112 |
| 4,455,690 | 6/1984 | Homsy | 3/1 |
| 4,470,941 | 9/1984 | Kurtz | 264/136 |
| 4,610,688 | 9/1986 | Silvestrini et al. | 623/1 |

FOREIGN PATENT DOCUMENTS

| | | | |
|---|---|---|---|
| 0051954 | 5/1982 | European Pat. Off. | |
| 3216005 | 11/1983 | Fed. Rep. of Germany | |
| 2387028 | 11/1978 | France | |
| 1602834 | 11/1981 | United Kingdom | 623/13 |

OTHER PUBLICATIONS

Pierre Rey et al., "New Fiber for Ligament and Tendon Prosthesis", Transactions, American Society for Artificial Internal Organs, 1985, vol. XXXI, pp. 305–307.
R. Neugebauer et al.: "Histological and Biomechanical Evaluation of Ligament Replacement with Various Alloplastic Materials", Chemical Abstracts, vol. 99, No. 6, Aug. 8, 1983, p. 315, No. 43482v, Columbus, Ohio, US; & Chir. Forum Exp. Klin. Forsch. 1983, 115–119.
J. Bejui et al.: "Prothese Ligamentaire Fibres de Carbone", Revue de Chirurgie Orthopedique T. 68, No. 2, 1982.
Dahhan Ph. Léandri J. Rey P. Prothéses Ligamentaires et Tendineuses à base d'une Fibre Synthétique Nouvelle., Annales du Colloque CEFRACOR, Counsel of Europe, Strasbourg, Mar. 5–7, 1984.
Dahhan Ph. Léandri J. Rey P. Prothéses Ligamentaires et Tendineuses à base d'une Fibre Synthétique Nouvelle., Biomat 84, Codernac, Bordeaux, pp. 135–143.

*Primary Examiner*—Richard J. Apley
*Assistant Examiner*—Paul Prebilic
*Attorney, Agent, or Firm*—Sughrue, Mion, Zinn, Macpeak and Seas

[57] ABSTRACT

New prostheses for ligaments and tendons in humans or animals intended to replace deficient original organs and induce the growth of new-formed tissue, which tissue, in turn, replaces such a prosthesis and reconstitutes an analogue of the original organ, may comprise at least one strand of synthetic polyaramide fibres NOMEX (i.e. polymetaphenylene isophthalamide the fibres not having any having any protective element so that they are placed in direct contact with surrounding live tissues, as a result of which the growth of fibrous new-formed tissue is induced to replace the synthetic fibres which are at least partly eliminated.

13 Claims, 2 Drawing Sheets

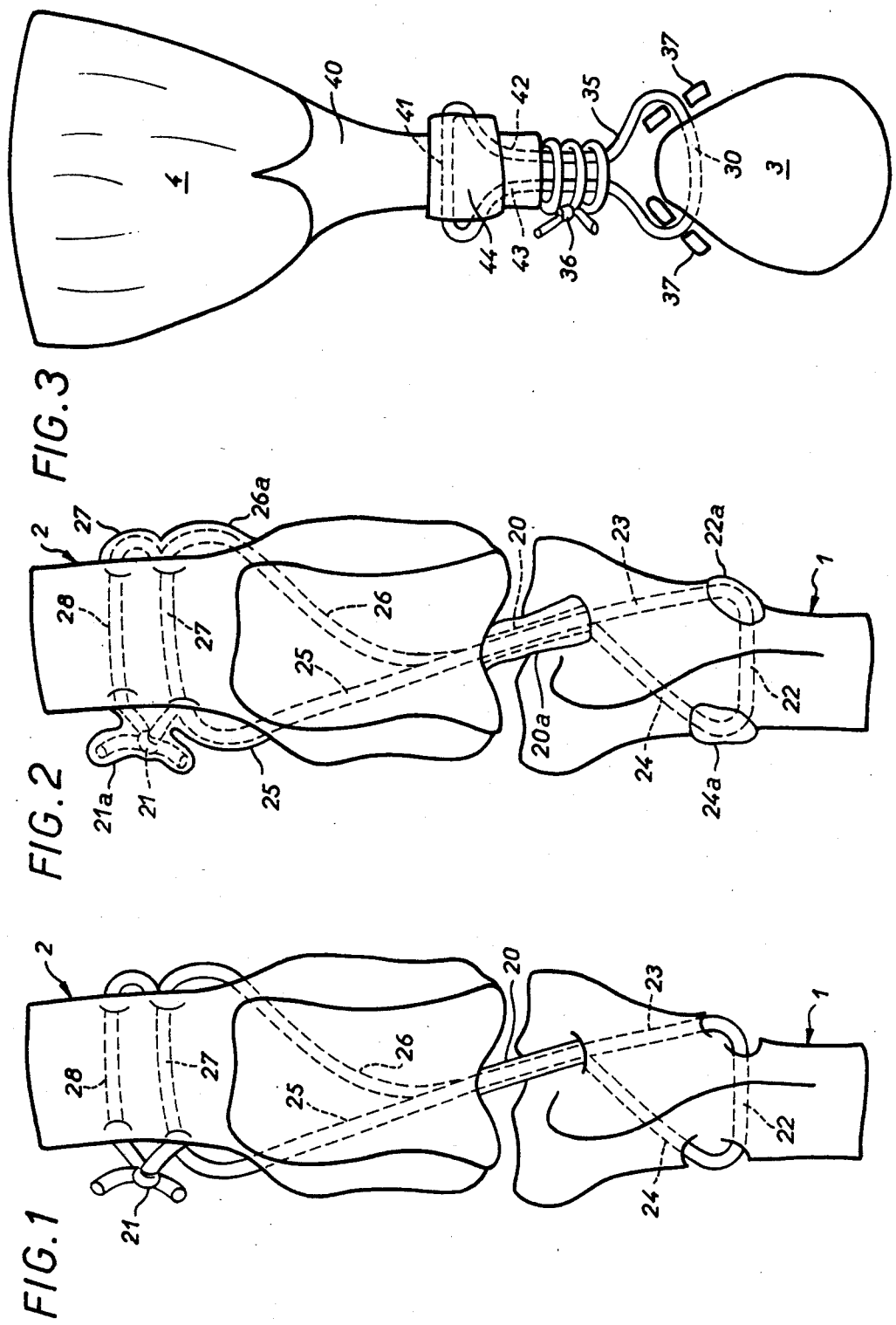

TEMPORARY PROSTHESIS FOR TENDONS AND LIGAMENTS, AND A METHOD OF FITTING SAME

The present invention relates to replacement prostheses, in particular ligamentary, tendinous, vascular and the like, and to permanent or temporary restorative prostheses, in particular stomatological, muscular and the like, produced from suitable fibres with a synthetic polymer basis.

The materials which have already been proposed for the production, in particular, of ligamentary and tendinous prostheses intended for implantation in an organism, include inter alia:
the following synthetic fibres:
  polyesters,
  polyethylene,
  polytetrafluoroethylene,
  polyamides, and
the following mineral fibres:
  steel fibres,
  carbon fibres.

However, on a biomechanical, anatomo-pathological, histological and clinical basis, after implantation of prosthetic ligaments and tendons the results obtained with the above-mentioned fibres have been mediocre and generally unsatisfactory.

With regard to ligamentary prostheses of pure carbon fibres, they have been abandoned after hopes had been raised of a large-scale application in clinical practice in the light of the following results, particularly in an intra-articular situation in dogs (cf. Revue de Chirurgie Orthopédique T. 68 No. 2-1982):

on a biomechanical basis, a rupture has been observed in all cases of prosthetic replacement of the anterior crucial knee ligament in dogs subjected to surgical intervention, thus showing beyond doubt that the mechanical properties of the implant are inadequate, despite a satisfactory clinical outcome;

on a anatamo-pathological basis, the majority of knees have manifested cartilaginous lesions of arthrotic nature, and on a histological basis the organism has manifested a cellular reaction of the "foreign body" type, namely a reaction of the numerous giant polynuclear cells of macrophagic type, known as Langhans' cells, which reaction does not correspond to solid tissue formation because of the great facility of dissociation of the cellular elements from one another; moreover, these cellular elements lead to the secondary formation of fibrous replacement tissue which is not sufficiently abundant to form a strong new ligament and which does not comprise fusiform connective cells which can be oriented in the same direction.

Likewise, steel fibre implants have not given good results, premature ruptures having been observed.

It is notable that the cellular reactions of the "foreign body" type lead to the formation of low-strength secondary tissues which are liable to compromise the normal operation of the prosthesis and to attack the fibres whose strength diminishes with time.

To prevent invasion of a tendinous prosthesis, U.S. Pat. No. 4,455,690 teaches the use of artificial tendons comprising a strand of longitudinal filaments of a biocompatible polymer, typically polyaramide NOMEX(R) forming a parallel sheet rolled and inserted into a sheath of another biocompatible polymer, typically porous polytetrafluoroethylene impregnated with a water-proofing resin which inhibits tissue rehabilitation. The stand is preferably lubricated with a dispersion of polytetrafluoroethylene. It is understood that the prosthesis is formed in this way so as to resist efficiently aggression and encroachment by adjacent tissues and to retain its original properties. Furthermore, the ends of the prosthesis are arranged to promote rehabilitation by spongy osseous tissue so as to ensure anchoring in the bone.

The invention relates to prostheses for ligaments and tendons which ensure temporarily the replacement of the natural organ and then induce the growth of new-formed tissue which reconstitutes an analogue of natural tissue.

For this purpose, the invention proposes a prosthesis for ligaments and tendons in humans or animals intended to replace a deficient original organ and to induce the growth of new-formed tissue which, in turn, replaces the prosthesis and reconstitutes an analogue of the original organ, comprising at least one strand of synthetic fibres of the class of polyaramides, said fibres not having any protective element so that they are placed in direct contact with surrounding live tissues, as a result of which the growth of fibrous new-formed tissue is induced to replace said synthetic fibres which are at least partly eliminated.

The invention additionally proposes methods of fitting prostheses for ligaments and tendons.

BRIEF DESCRIPTION OF THE DRAWINGS

FIG. 1 represents a prosthesis according to the invention, as a replacement of the anterior crucial ligament of a dog;

FIG. 2 illustrates diagrammatically the condition of the joint in the FIG. 1 after the growth of a new-formed ligament as a reaction to the prosthesis;

FIG. 3 illustrates diagrammatically the fitting of a prosthesis according to the invention to a sheep, as a replacement of the Achilles tendon, between the calcaneum and the mass of the soleus and gemellus muscles;

DETAILED DESCRIPTION OF THE INVENTION

Figure 4A:
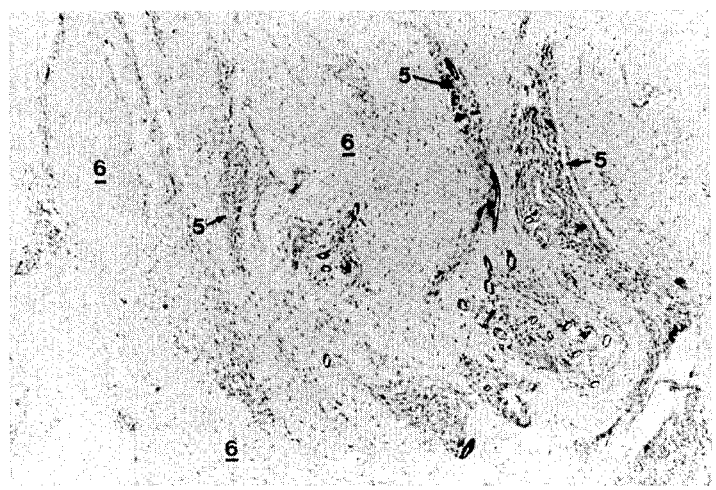
FIG. 4A is an histological view of the foreign body reaction induced in a dog after implantation of a ligamentary prosthesis according to the invention, with magnification $\times 10$.

Our experimentation with a view to replacing the fibres used in the state of the art to provide ligamentary or tendinous prostheses has led us to the use of a synthetic fibre known under the trade mark "NOMEX", marketed by the firm Dupont de Nemours, and used in the industry as an upholstery material or for the manufacture of safety clothing, in particular to replace asbestos.

NOMEX is a polyarylamide obtained by polycondensation of metaphenylene diamine and isophthalic acid.

With a view to its clinical utilisation, the filaments or strands of "NOMEX" fibres are first degreased so as to remove particles of grease used during spinning. This degreasing operation is carried out by immersion in a bath of boiling trichloroethylene, followed with drying by hot evaporation.

Biological tolerance was evaluated by anatopathological inspection after implantating bundles of "NOMEX" fibres, previously degreased, under the abdominal skin of a particular number of rabbits.

Subsequently, the Achilles tendon was replaced, in sheep, using braids or strands of "NOMEX" fibres, previously degreased, and the anterior crucial ligament in a certain number of dogs of the Beagle breed.

The results, at approximately two years after the surgical operations indicated above, are set out in the following.

From the clinical aspect, there was noted, particularly for the prosthetic Achilles tendon, normal recovery of walking, running and jumping activity; the clinical results were also good in the ligamentary prostheses.

From the biomechanical aspect, there was observed a very slight diminution in strength of the fibre used, which decreased from 56.5 kg/mm$^2$ to 55.2 kg/mm$^2$ (as revealed by strength tests), which represents a decrease of about barely 2.3%, notably in the case of the rabbit one year after implantation.

From the histological aspect, the foreign body reaction induces secondarily an abundant fibrous reaction which produces strong tissue capable of having a satisfactory prosthetic function.

It will be appreciated that hitherto research was essentially concerned with prosthetic materials which were considered to be permanent, whether linear polyamides such as NYLON(®), polyesters such as DACRON(®), polytetrafluoroethylenes such as GORE TEX(®), or carbon fibres; in this case a minimum of histological reactions is desired since the new-formed tissues appear to be insufficiently tenacious for long-term replacement of the prosthesis. Now it has been established that none of the above-mentioned prosthetic materials exhibited sufficiently durable resistance to attack by the foreign body reaction (in terms of several years).

In particular, parallel to the tests according to the invention, tests have been carried out with prostheses made of carbon fibre for replacement of the anterior crucial ligament in dogs of the Beagle breed. In histological inspections of these prostheses, the carbon fibres appear as more or less fragmented rods, cut substantially longitudinally and enveloped in masses of tissue corresponding to a specific inflammatory fibrous reaction of the "foreign body" type, which is very rich in giant polynuclear cells known as Langhans' cells; fibrous development from this cellular reaction is weak and the new-formed tissue is of low mechanical strength.

The prosthesis for the anterior crucial ligament represented in FIG. 1, which is fitted between the top end of the tibia 1 and the bottom end of the femur 2 to maintain the support of the condyles of the femur 2 on the tibial head, comprises a strand or braid 20 of "NOMEX" fibres. The strand 20 is inserted in three ducts provided in the tibia, a transverse duct 22 and two oblique ducts 23 and 24 which through the same orifice emerge at the location of insertion of the original ligament at the head of the tibia. The two filaments of the strand 20 follow side by side the natural path of the anterior crucial ligament and penetrate into two oblique ducts 25 and 26 provided in the femur 2, which diverge from the location of insertion of the crucial ligament on the femur and, crossing one another, pass through two transverse ducts 27 and 28 formed in the femur 2 above the condyles. Finally, the two filaments are reunited by a ligature knot 21.

As illustrated diagrammatically in FIG. 2, the reaction of the living tissues which are in contact with the "NOMEX" fibres induces the formation of a fibrous sheath 20a around the strand 20 along its path following that of the original ligament, this fibrous sheath reconstituting a new-formed ligament, whereas the "NOMEX" fibres are at least partly resorbed. Furthermore, in the passages of the ducts 22, 23, 24, 25, 26, 27 and 28 the growth of spongy bone will encroach on the strand of fibres and thus ensure strong anchorage.

Moreover, at the points where the strand emerges between the ducts, this strand becomes imprisoned in new-formed tissue 23a, 24a, 25a, 26a, 27a and also 21a around the ligature knot 21.

The Achilles tendon prosthesis illustrated in FIG. 3, in the case of a sheep, connects the calcaneum 3 to the group of soleus' and gemellus muscles 4. A strand of "NOMEX" fibres passes into a duct 30 provided in the calcaneum 3. The two filaments of the strand 35 are passed into ducts 41, 42 and 43 provided in the stump 40 of the Achilles tendon maintained upon insertion in the muscular masses. Following this, the filaments of the strand 35 are wound around lengths between the calcaneum 3 and the stump 40 to form a knotted ligature 36. It will be noted that at the opening of the ducts 30 and 41, 42, 43 there are arranged small plates 37, 44 of rhodergon (®) so as to prevent, firstly, sharp angles in the strand at the opening of the ducts and, secondly, so as to improve the quality of the anchoring of the prosthesis in the calcaneum 3 and tendon stump 40, by osseous or tendinous rehabilitation.

The bare portions of the strand 35 of "NOMEX" fibres will be covered, as result of the reactions of live tissues in contact therewith, by a fibrous sheath which will reconstitute an Achilles tendon, and the "NOMEX" fibres will be at least partly resorbed.

FIG. 4A shows the histological view of the foreign body reaction induced in a dog after implantation of a prosthetic ligament of "NOMEX" fibres, in accordance with the invention.

Here and there it is possible to discern isolated zones 5 of macrophagic reaction enclosed within a dominant zone 6 of fibrous tissue, induced by the macrophagic reaction : more precisely, the macrophages mobilised by the organism against the ligamentary prosthesis according to the invention surround the synthetic fibres so as to dissociate the adjacent fibres and progressively destroy them so as to make room for the thick, strong fibrous tissue 6.

Figure 4B:
FIG. 4B is an histological view corresponding to FIG. 4A, with magnification $\times 120$.

In FIG. 4B it is possible to discern on a larger scale (magnification equal to 120) masses 7 corresponding to the fibrous reaction caused by the macrophages 8 and which takes place in contact with "NOMEX" fibres 9, these macrophages 8 being charged with macrophagic synthetic elements.

Figure 5:
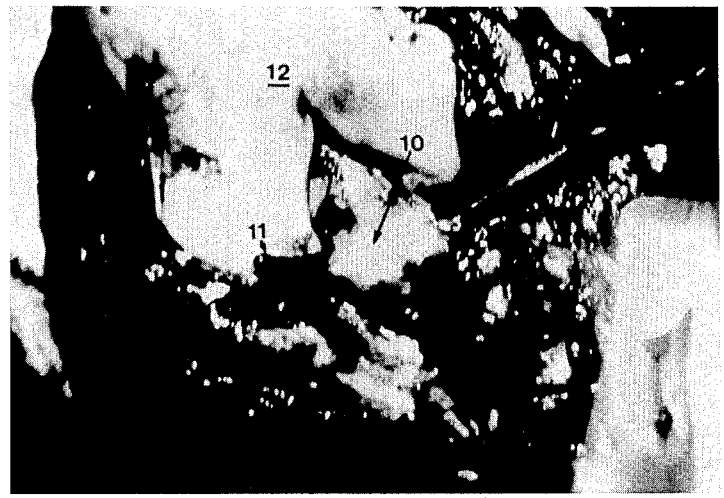
FIG. 5 is a macroscopic view corresponding to FIGS. 4A and 4B.

On a histological and anatomical basis (microscopic and macroscopic view) a ligamentary prosthesis according to the invention has an aspect very close to that of a natural ligament: to this end it is very interesting to observe the new-formed anterior crucial ligament 10 in an intra-articular situation in a dog, as shown in FIG. 5 in which it is raised by means of a surgical clip 11 and attached to the femur 12: the replacement tissue is thick and of bright fibrous aspect (a natural ligament would have been less thick but of similar aspect).

With regard to intra-osseous anchoring, the latter takes place in each case by rehabilitation of the prosthesis according to the invention with a cellulo-fibrous tissue which penetrates the fibres and unites them with the neighbouring osseous reaction.

What is claim is:

1. A prosthesis for humans or animals for replacing a deficient original ligament or tendon, the prosthesis comprising at least one strand of degreased poly(metaphenylene isophthalamide) fibers said at least one strand being externally exposed and devoid of external protection and thus adapted to come into direct contact with live tissues when the prosthesis is implanted, whereby reactions of surrounding tissues induce growth of fibrous new-formed tissue to replace and eliminate at least in part the poly(metaphenylene isophthalamide) fibers.

2. A prosthesis according to claim 1, wherein said at least one strand consists essentially of poly(metaphenylene isophthalamide) fibers.

3. A prosthesis according to claim 1, wherein said at least one strand comprises mainly poly(metaphenylene isophthalamide) fibers.

4. A method for replacing of a ligament between two bones of a joint in humans or animals, comprising the steps of preparing at least one exposed strand of poly(metaphenylene isophthalamide)fibers without any protective coating or covering to form a prosthesis, arranging the strand along the natural path of a original ligament and attaching the strand to both bones whereby reactions of surrounding tissues induce growth of fibrous new-formed tissue to replace and eliminate at least in part the poly(metaphenylene isophthalamide) fibers of the prosthesis.

5. A method according to claim 4, further comprising the step of degreasing the poly(metaphenylene isophthalamide) fibers before implantation of the prosthesis.

6. A method according to claim 5, wherein the degreasing step comprises immersing the poly(metaphenylene isophthalamide) fibers in boiling trichloroethylene and then drying them.

7. A method according to claim 4, wherein said at least one strand consists essentially of poly(metaphenylene isophthalamide) fibers.

8. A method according to claim 4, wherein said at least one strand comprises mainly poly(metaphenylene isophthalamide) fibers.

9. A method for replacing of a tendon between a muscle and a bone in humans or animals, the method comprising the steps of preparing at least one expressed strand of poly(metaphenylene isophthalamide) fibers without any protective coating or covering to form a prosthesis, arranging the prosthesis along the natural path of the original tendon between the bone and a stump of the original tendon attached to the muscle and attaching the prosthesis to the bone and the stump whereby reactions of surrounding tissues induce growth of fibrous new-formed tissue to replace and eliminate at least in part the poly(metaphenylene isophthalamide) fibers of the prosthesis.

10. A method according to claim 9, further comprising the step of degreasing poly(metaphenylene isophthalamide) fibers before implantation of the prosthesis.

11. A method according to claim 10, wherein the degreasing step comprising immersing the poly(metaphenylene isophthalamide) fibers in boiling trichloroethylene and then drying them.

12. A method according to claim 9, wherein said at least one strand consists essentially of poly(metaphenylene isophthalamide) fibers.

13. A method according to claim 9, wherein at least one strand comprises mainly poly(metaphenylene isophthalamide) fibers.

* * * * *

UNITED STATES PATENT AND TRADEMARK OFFICE
CERTIFICATE OF CORRECTION

PATENT NO. :     4,804,383

DATED      :     February 14, 1989

INVENTOR(S) :    Pierre REY, Jacqueline LEANDRI, Philippe DAHHAN

It is certified that error appears in the above-identified patent and that said Letters Patent is hereby corrected as shown below:

On the title page, item [76]:

"Pierre Rey, 18 rue Aristide Briand, 77400 Lagny"

to read

--Pierre Rey, 18 rue Aristide Briand, 77400 Thorigny--

Signed and Sealed this

Twelfth Day of June, 1990

Attest:

HARRY F. MANBECK, JR.

*Attesting Officer*              *Commissioner of Patents and Trademarks*